United States Patent [19]

Bergstrand et al.

[11] Patent Number: 5,817,338
[45] Date of Patent: Oct. 6, 1998

[54] MULTIPLE UNIT TABLETED DOSAGE FORM OF OMEPRAZOLE

[75] Inventors: Pontus John Arvid Bergstrand, Göteborg; Kurt Ingmar Lövgren, Mölndal, both of Sweden

[73] Assignee: Astra Aktiebolag, Sodertalje, Sweden

[21] Appl. No.: 454,395

[22] PCT Filed: Jun. 7, 1995

[86] PCT No.: PCT/SE95/00677

§ 371 Date: Jun. 20, 1995

§ 102(e) Date: Jun. 20, 1995

[87] PCT Pub. No.: WO96/01623

PCT Pub. Date: Jan. 25, 1996

[30] Foreign Application Priority Data

Jul. 8, 1994 [SE] Sweden .................................. 9402432
Jul. 8, 1994 [SE] Sweden .................................. 9402433

[51] Int. Cl.⁶ .............................. A61K 9/22; A61K 9/30
[52] U.S. Cl. .................... 424/468; 424/465; 424/467; 424/469; 424/490; 424/475; 514/925
[58] Field of Search ..................... 424/465, 464, 424/468, 469, 470, 461, 462, 479, 480, 482, 493, 494, 497, 490

[56] References Cited

U.S. PATENT DOCUMENTS

| 4,786,505 | 11/1988 | Lovgren et al. | 424/468 |
| 4,853,230 | 8/1989 | Lövgren et al. | 424/466 |
| 4,927,640 | 5/1990 | Dahlinder et al. | 424/497 |

FOREIGN PATENT DOCUMENTS

| 0008780 | 8/1979 | European Pat. Off. . |
| 0005129 | 4/1981 | European Pat. Off. . |
| 0072021 | 8/1982 | European Pat. Off. . |
| 0080341 | 11/1982 | European Pat. Off. . |
| 0080341 | 6/1983 | European Pat. Off. . |
| 0108295 | 10/1983 | European Pat. Off. . |
| 0108504 | 10/1983 | European Pat. Off. . |
| 0111103 | 10/1983 | European Pat. Off. . |
| 0170752 | 12/1984 | European Pat. Off. . |
| 0124495 | 1/1987 | European Pat. Off. . |
| 0013566 | 1/1990 | European Pat. Off. . |
| 0391518 | 2/1990 | European Pat. Off. . |
| 0541369 | 11/1992 | European Pat. Off. . |
| 0587220 | 8/1993 | European Pat. Off. . |
| 0365947 | 7/1994 | European Pat. Off. . |
| 0648487 | 10/1994 | European Pat. Off. . |
| 0247983 | 12/1994 | European Pat. Off. . |
| 0519144 | 12/1994 | European Pat. Off. . |
| 2066070 | 12/1980 | United Kingdom . |
| 2091097 | 11/1981 | United Kingdom . |
| 2132887 | 11/1983 | United Kingdom . |
| 2285989 | 1/1995 | United Kingdom . |
| 8501207 | 9/1984 | WIPO . |
| 8503436 | 2/1985 | WIPO . |
| 8702240 | 9/1986 | WIPO . |
| 9006925 | 6/1990 | WIPO . |
| 9119712 | 12/1991 | WIPO . |
| 9222284 | 12/1992 | WIPO . |
| 9312772 | 12/1992 | WIPO . |
| 9403160 | 7/1993 | WIPO . |
| 9427988 | 12/1994 | WIPO . |
| 9501783 | 1/1995 | WIPO . |
| 9501977 | 1/1995 | WIPO . |
| 9510264 | 4/1995 | WIPO . |
| 9601623 | 6/1995 | WIPO . |
| 9601625 | 1/1996 | WIPO . |

OTHER PUBLICATIONS

Pharmaceutical Research, vol. 10 (1993), p. S–274.
Drugs Made in Germany, 37, No. 2 (1994), pp.53–60.
Aulton M.E. (Churchill Livingston) Pharmaceutics: The Science of Dosage Form Design (1988), pp. 316–321.

*Primary Examiner*—Thurman K. Page
*Assistant Examiner*—James M. Spear
*Attorney, Agent, or Firm*—White & Case L.L.P.

[57] ABSTRACT

A new pharmaceutical multiple unit tableted dosage form containing omeprazole or one of its single enantiomers or an alkaline salt of omeprazole or one of its single enantiomers, a method for the manufacture of such a formulation, and the use of such a formulation in medicine.

25 Claims, No Drawings

MULTIPLE UNIT TABLETED DOSAGE FORM OF OMEPRAZOLE

This application is a 371 of PCT/SE95/00677 filed Jun. 7, 1995.

FIELD OF THE INVENTION

The present invention is related to new pharmaceutical preparations in the form of a multiple unit tableted dosage form comprising omeprazole or one of its single enantiomers or an alkaline salt of omeprazole or one of its single enantiomers. The novel tableted dosage form is intended for oral use. Furthermore, the present invention refers to a method for the manufacture of such preparations and, to the use of such preparations in medicine.

BACKGROUND OF THE INVENTION

The compound known under the generic name omeprazole, 5-methoxy-2[[(4-methoxy-3,5-dimethyl-2-pyridinyl)methyl]sulfinyl]-1H-benzimidazole, is disclosed i.a. in EP-A1-0 005 129. Certain salts of omeprazole including alkaline salts of omeprazole are described in EP-A1- 0 124 495 and in WO 95/01977. Novel salts of the single enantiomers of omeprazole are described in WO 94/27988.

Omeprazole or one of its single enantiomers or alkaline salts thereof, in the following stated shortly as omeprazole, are useful for inhibiting gastric acid secretion in mammals and man. In a more general sense, said substances may be used for prevention and treatment of gastric acid related diseases in mammals and man, including e.g. reflux esophagitis, gastritis, duodenitis, gastric ulcer and duodenal ulcer. Furthermore, omeprazole may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. Omeprazole may also be used in patients in intensive care situations, in patients with acute upper gastrointestinal bleeding, pre- and postoperatively to prevent acid aspiration of gastric acid and to prevent and treat stress ulceration. Further, omeprazole may be useful in the treatment of psoriasis as well as in the treatment of Helicobacter infections and diseases related to these.

Omeprazole is, however, susceptible to degradation/transformation in acidic and neutral media. The half-life of degradation of omeprazole in water solutions at pH-values less than three is shorter than ten minutes. The degradation of omeprazole is catalyzed by acidic compounds and is stabilized in mixtures with alkaline compounds. The stability of omeprazole is also affected by moisture, heat, organic solvents and to some degree by light.

In respect to the stability properties of omeprazole, it is obvious that omeprazole in an oral solid dosage form must be protected from contact with the acidic gastric juice and the active substance must be transferred in intact form to that part of the gastrointestinal tract where pH is near neutral and where rapid absorption of omeprazole can occur.

A pharmaceutical oral dosage form of omeprazole is best protected from contact with acidic gastric juice by an enteric coating layer. In U.S. Pat. No. 4,786,505 such an enteric coated omeprazole preparation is described. Said omeprazole preparation contains an alkaline core comprising omeprazole, a separating layer and an enteric coating layer. In order to further enhance the stability during storage the prepared formulation may optionally be packed with a desiccant.

The hard gelatine capsules containing an enteric coated pellet formulation of omeprazole marketed by the Applicant today, are not suitable for press-through blister packages. Thus, there has been a demand for development of new enteric coating layered multiple unit preparations of omeprazole with good chemical stability as well as improved mechanical stability making it possible to produce well functioning and patient-friendly packages. Furthermore, there is a demand for omeprazole formulations having improved patient acceptance, such as divisible and/or dispersible tablets.

An improved mechanical stability can be obtained with an enteric coating layered tablet for example as described in WO 95/01783. However, only an enteric coating layered multiple units tablet can be made divisible and dispersible. A further advantage of a multiple unit dosage form is that it disperses into a multitude of small units in the stomach upon administration.

Prior art discloses many different types of multiple unit dosage forms. Usually this type of formulation is requested for controlled release formulations, such as sustained release formulations. Typically, the multiple unit formulation may be a tablet which disintegrates in the stomach to make available a multitude of coated units, or pellets filled in a capsule. (See for example EP 0 080 341 and U.S. Pat. No. 4,786,505).

An example to obtain a controlled release dosage form releasing the active substance by diffusion through a membrane is described in U.S. Pat. No. 4,927,640, i.e. a multiple-unit system containing small inert cores coated with active substance and a release controlling polymeric membrane. The mechanical properties of such multiple units formulated into tablets are reported in Pharmaceutical Research, 10 (1993), p.S-274. Other examples of controlled release dosage forms are for example described in Aulton M. E. (Churchill Livingstone), Pharmaceutics: The science of dosage form design (1988), p. 316–321.

Even if the specification of U.S. Pat. No. 4,786,505 under the subtitle Final dosage form mentions that the manufactured pellets may be formulated into tablets there are no examples describing any compositions of such a tablet formulation or a technique to manufacture such a formulation. In practice, problems arise when enteric coating layered pellets containing acidic susceptible benzimidazoles as active substance are compressed into tablets. If the enteric coating layer does not withstand the compression of the pellets into a tablet the susceptible active substance will be destroyed by penetrating acidic gastric juice, i.e. the acid resistance of the enteric coating layer of the pellets will not be sufficient in the tablet after compression. The above described problems are well illustrated in Reference Examples below.

Further, controlled release tablets from enteric coated particles are described in Drugs Made In Germany, 37 No. 2 (1994), p. 53. The teaching in this reference is that a combination of a methacrylic acid copolymer (L30D-55) and a copolymer of ethyl acrylate and methyl methacrylate (NE30D) is suitable as coating polymers for enteric coated particles compressed into tablets. Reference Example II shows that this recommendation is not applicable when formulating multiple unit tableted dosage forms of the acidic susceptible substance omeprazole. The acid resistance of the pellets compressed into a tablet is too low. The cited reference Drugs Made In Germany also states that the use of the copolymer L30D-55 without the addition of the copolymer NE30D as material for enteric coating layers will result in coated pellets which cannot withstand compression forces used during the tableting process. With reference to this statement it is surprisingly found that pellets covered with L30D-55 according to this invention, see Examples below, are possible to compress into tablets with fulfilled requirements including acceptable acid resistance of the tablet.

The Applicant is not aware of any working example in the prior art of a multiple unit tableted dosage form comprising an acidic susceptible benzimidazole compound, such as omeprazole.

DESCRIPTION OF THE INVENTION

The Applicant has now surprisingly found that tablets according to the present invention comprising enteric coating layered units containing an acidic susceptible substance in the form of omeprazole or one of its single enantiomers or an alkaline salt thereof can be manufactured by compressing said units into tablets without significantly affecting the properties of the enteric coating layer. As explained above, if the enteric coating layer is damaged during compression of the enteric coating layered units, the acid resistance of said enteric coating layer in the manufactured tablet will not be sufficient, and the manufactured tablets will not fulfill standard requirements on enteric coated articles, such as e.g. those defined in the United States Pharmacopeia, (USP), hereby incorporated in a whole by reference. In the following the expression "omeprazole" is used alternatively with the more complete expression "omeprazole, one of its single enantiomers, an alkaline salt of omeprazole or one of its single enantiomers" for defining the active substance.

One object of the present invention is to provide a pharmaceutical multiple unit tableted dosage form comprising omeprazole or one of its single enantiomers or an alkaline salt of omeprazole or one of its single enantiomers, in which the active substance is in the form of individually enteric coating layered units compressed into a tablet. The enteric coating layer(s) covering the individual units of active substance has properties such that the compression of the units into a tablet does not significantly affect the acid resistance of the individually enteric coating layered units. The active substance is prevented from degradation and dissolution in acidic media and has a good stability during long-term storage. The enteric coating layer covering the individual units disintegrates/dissolves rapidly in near neutral or alkaline media.

Another object of the present invention is to provide a pharmaceutical multiple unit tableted dosage form comprising omeprazole or one of its single enantiomers or an alkaline salt of omeprazole or one of its single enantiomers which is suitable for press-through blister packages and which also has an improved patient acceptance.

A further object of the present invention is to provide a multiple unit tableted dosage form comprising omeprazole or one of its single enantiomers or an alkaline salt of omeprazole or one of its single enantiomers, which is divisible and easy to handle. The multiple unit tableted dosage form may be dispersed in an aqueous liquid and can be given to patients with swallowing disorders and in pediatrics. Such a suspension of dispersed omeprazole units of appropriate size can be used for oral administration and also for feeding through a naso-gastric tube.

DETAILED DESCRIPTION OF THE INVENTION

The novel multiple unit tableted dosage form comprising omeprazole or one of its single enantiomers or an alkaline salt of omeprazole or one of its single enantiomers is characterized in the following way. Individually enteric coating layered units containing omeprazole or one of its single enantiomers or an alkaline salt of omeprazole or one of its single enantiomers, and optionally alkaline substances, are mixed with tablet excipients and compressed into multiple unit tableted dosage forms. With the expression "individual units" is meant small beads, particles, granules or pellets, in the following referred to as pellets.

The compaction process (compression) for formulating the multiple unit tableted dosage form must not significantly affect the add resistance of the enteric coating layered pellets. In other words the mechanical properties, such as the flexibility and hardness as well as the thickness, of the enteric coating layer(s) must secure that the requirements on enteric coated articles in the United States Pharmacopeia are accomplished and that the acid resistance does not decrease more than 10% during the compression of pellets into tablets.

The flexibility/hardness of enteric coating layers can be characterized for instance as Vickers hardness measured with a Shimadzu micro hardness indentation tester type HMV 2 000.

The acid resistance is defined as the amount of active substance in tablets or pellets after being exposed to simulated gastric fluid, USP, or to 0.1M HCl(aq) relative to that of unexposed tablets or pellets, respectively. The test is accomplished in the following way. Tablets or pellets are exposed to simulated gastric fluid at a temperature of 37° C. The tablets disintegrate and release the enteric coating layered pellets to the medium. After two hours the enteric coating layered pellets are removed and analyzed for omeprazole content using High Performance Liquid Chromatography (HPLC). Presented values of acid resistance are averages of at least three individual determinations.

Core Material

The core material for the individually enteric coating layered pellets can be constituted according to different principles. Seeds layered with active substance in the form of omeprazole or one of its single enantiomers or an alkaline salt of omeprazole or one of its single enantiomers, optionally mixed with alkaline reacting compounds, can be used as the core material for the further processing.

The seeds, which are to be layered with the active substance, can be water insoluble seeds comprising different oxides, celluloses, organic polymers and other materials, alone or in mixtures or water soluble seeds comprising different inorganic salts, sugars, non-pareils and other materials, alone or in mixtures. Further, the seeds may comprise active substance in the form of crystals, agglomerates, compacts etc. The size of the seeds is not essential for the present invention but may vary between approximately 0.1 and 2 mm. The seeds layered with active substance are produced either by powder or solution/suspension layering using for instance granulating or spray coating/layering equipment.

Before the seeds are layered, the active substance may be mixed with further components. Such components can be binders, surfactants, fillers, disintegrating agents, alkaline additives or other pharmaceutically acceptable ingredients, alone or in mixtures. The binders are for example celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants are found in the groups of pharmaceutically acceptable non-ionic or ionic surfactants such as for instance sodium lauryl sulfate.

Alternatively, omeprazole optionally mixed with alkaline compounds and further mixed with suitable constituents can be formulated into core material. Said core materials may be produced by extrusion/spheronization, balling or compression utilizing different process equipments. The size of the formulated core materials is approximately between 0.1 and 4 mm and preferably between 0.1 and 2 mm. The manufactured core materials can further be layered with additional ingredients comprising active substance and/or be used for further processing.

The active substance is mixed with pharmaceutical constituents to obtain preferred handling and processing properties and a suitable concentration of the active substance in the final mixture. Pharmaceutical constituents such as fillers, binders, lubricants, disintegrating agents, surfactants and other pharmaceutically acceptable additives, can be used.

The active substance may also be mixed with an alkaline pharmaceutically acceptable substance (or substances). Such substances can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane, basic amino acids and their salts or other similar, pharmaceutically acceptable pH-buffering substances.

Alternatively, the aforementioned core material can be prepared by using spray drying or spray congealing technique.

The active substance is in the form of omeprazole or one of its single enantiomers or an alkaline salt of omeprazole or one of its single enantiomers. Omeprazole has an asymmetric centre in the sulfur atom, i.e. exists as two optical isomers (enantiomers). Both the pure enantiomers, racemic mixtures (50% of each enantiomer) and unequal mixtures of the two enantiomers are suitable for the pharmaceutical formulation according to the present invention. A suitable form of omeprazole for preparation of the new multiple unit tableted dosage form according to the present invention can be the magnesium salt of omeprazole with a specific degree of crystallinity and other physical properties disclosed in WO 95/01977, hereby incorporated in a whole by reference. Said magnesium omeprazole product has a degree of crystallinity which is higher than 70% and preferably higher than 75% as determined by X-ray powder diffraction. Other suitable forms of the active substance are the sodium, potassium, magnesium and calcium salts of the single enantiomers of omeprazole, especially in their crystalline form described in WO 94/27988, hereby incorporated in a whole by reference.

Enteric Coating Layer(s)

Before applying enteric coating layer(s) onto the core material in the form of individual pellets, said pellets may optionally be covered with one or more separating layers comprising pharmaceutical excipients optionally including alkaline compounds such as for instance pH-buffering compounds. This/these separating layer(s) separate(s) the core material from the outer layer(s) being enteric coating layer(s).

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the separating layer(s).

When the optional separating layer(s) is applied to the core material it may constitute a variable thickness. The maximum thickness of the optional separating layer(s) is normally only limited by processing conditions. The separating layer(s) may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminium hydroxide/sodium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof. Talc or other compounds may be added to increase the thickness of the layer(s) and thereby strengthen the diffusion barrier. The optionally applied separating layer (s) is not essential for the invention. However the separating layer(s) may improve the chemical stability of the active substance and/or the physical properties of the novel multiple unit tableted dosage form.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s).

The enteric coating layers contain pharmaceutically acceptable plasticizers to obtain the desired mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during the compression of pellets into tablets. The amount of plasticizer is usually above 10% by weight of the enteric coating layer polymer(s), preferably 15–50%, and more preferably 20–50%. Additives such as dispersants, colorants, pigments, polymers e.g. poly (ethylacrylat, methylmethacrylat), anti-tacking and anti-foaming agents may also be included into the enteric coating layer(s). Other compounds may be added to increase film thickness and to decrease diffusion of acidic gastric juices into the add susceptible material.

To protect an acidic susceptible substance in the form of omeprazole or one of its single enantiomers or an alkaline salt of omeprazole or one of its single enantiomers and to obtain an acceptable acid resistance of the multiple unit tableted dosage form according to the invention, the enteric coating layer(s) constitutes a thickness of approximately at least 10 µm, preferably more than 20 µm. The maximum thickness of the applied enteric coating layer(s) is normally only limited by processing conditions.

Over-Coating Layer

Pellets covered with enteric coating layer(s) may further be covered with one or more over-coating layer(s). The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the over-coating layer(s). Said over-coating layer may further prevent potential agglomeration of enteric coating layered pellets, further protect the enteric coating layer towards cracking during the compaction process and enhance the tableting process. The maximum thickness of the applied over-coating layer(s) is normally only limited by processing conditions.

Tablets

The enteric coating layered pellets are mixed with tablet excipients and compressed into a multiple unit tableted dosage form according to the present invention. The enteric coating layered pellets with or without an over-coating layer are mixed with tablet excipients such as fillers, binders, disintegrants, lubricants and other pharmaceutically acceptable additives and compressed into tablets. The compressed tablet is optionally covered with filmforming agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance.

The amount of enteric coating layered pellets constitutes less than 75% by weight of the total tablet weight and preferably less than 60%. By choosing small enteric coating layered pellets in the formulation according to the present invention, the number of pellets in each tablet can be held high which in turn makes the tablet divisible with retained dosing accuracy.

The mechanical properties, i.e. the flexibility and hardness of the enteric coating layer are essential for the acid resistance of the multiple unit tableted dosage form. The flexibility/hardness of the enteric coating layer surface may be characterized as a preliminary process parameter in the form of Vickers hardness, measured on enteric coating layered pellet(s) before compression of said pellets into tablets. The Vickers hardness may be measured with a Shimadzu micro hardness indentation tester type HMV 2000 (Micro Hardness Testing Machines for Vickers and Knoop Hardness JIS B 7734-1984 and JIS Z 2251-1980). The ability of the enteric coating layer(s) to withstand compression into tablets is, of course, a function of both the amount of applied coating layer and the mechanical properties of said coating material. To obtain well functioning enteric coating layered pellets with a reasonable amount of enteric coating layer material and which pellets can be compressed into tablets without significantly affecting the add resistance, an enteric coating layer surface with a Vickers hardness of less than 8 is preferred. In case the pellets are covered with an over-coating layer the Vickers hardness of the enteric coating layer must be characterized before the over-coating layer is applied. A harder over-coating layer (Vickers hardness higher than 8) can be applied on top of a flexible and softer (Vickers hardness less than 8) enteric coating layer with retained acid resistance during compaction.

Thus, the formulation according to the invention consists of core material containing active substance in the form of omeprazole or one of its single enantiomers or an alkaline salt of omeprazole or one of its single enantiomers, optionally mixed with alkaline compound(s), and excipients. The addition of an alkaline material may not be necessary, but such a substance may further enhance the stability of the active substance. The core material is optionally covered with one or more separating layer(s) optionally containing alkaline substance(s). The pellets, optionally covered with a separating layer(s), are then covered with one or more enteric coating layer(s) making the pellets insoluble in acidic media, but disintegrating/dissolving in near neutral to alkaline media such as, for instance the liquids present in the proximal part of the small intestine, the site where dissolution is wanted. The enteric coating layered pellets may further be covered with an over-coating layer before being formulated into the multiple unit tableted dosage form.

Process

The process for the manufacture of the dosage form represents a further aspect of the invention. The pharmaceutical processes can preferably be completely water-based and there are different descriptions given in the accompanying examples below.

Use of Preparation

The preparation according to the invention is especially advantageous in reducing gastric acid secretion. Such a multiple unit tableted dosage form is administered one to several times a day. The typical daily dose of the active substance varies and will depend on various factors such as the individual requirements of the patients, the mode of administration and the disease. In general the daily dose will be in the range of 1–400 mg of active substance, i.e. omeprazole or one of its single enantiomers or alkaline salts thereof.

The preparation according to the present invention is also suitable for dispersion in an aqueous liquid with neutral or slightly acidic pH-value before being orally administered or fed through a naso-gastric tube.

Multiple unit tableted dosage forms of omeprazole according to the present invention have been tested in humans.

The invention is illustrated more in detail by the following examples.

EXAMPLES

Example 1

| Core material | |
|---|---|
| Magnesium omeprazole | 600 g |
| Mannitol | 1000 g |
| Microcrystalline cellulose | 300 g |
| Hydroxypropyl cellulose | 100 g |
| Sodium lauryl sulfate | 6 g |
| Purified water | 802 g |
| Separating layer | |
| Core material | 400 g |
| Hydroxypropyl methylcellulose | 48 g |
| Purified water | 960 g |
| Enteric coating layer | |
| Pellets covered with separating layer | 200 g |
| Methacrylic acid copolymer | 100 g |
| Triethyl citrate | 30 g |
| Mono- and diglycerides | 5 g |
| Polysorbate 80 | 0.5 g |
| Purified water | 309 g |
| Tablets | |
| Enteric coating layered pellets | 200 g |
| Microcrystalline cellulose | 299 g |
| Sodium stearyl fumarate | 1.2 g |

Sodium lauryl sulfate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed.

The wet mass is forced through an extruder equipped with screens, aperture size 0.5 mm. The extrudate is spheronized on a friction plate in a spheronizing apparatus. The core material is dried in a fluid bed dryer and classified. The prepared core material is covered with separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus. The Vickers hardness of enteric coating layered pellets prepared is measured to a value of 2.

Enteric coating layered pellets, microcrystalline cellulose and sodium stearyl fumarate are mixed and compressed into tablets with a tablet weight corresponding to 20 mg omeprazole, using a single punch tableting machine equipped with 10 mm round punches. Tablets with a hardness of 110–120N (Schleuniger hardness tester) are produced.

Example 2

| Core material | |
|---|---|
| Magnesium omeprazole | 15.0 kg |
| Sugar sphere seeds | 15.0 kg |
| Hydroxypropyl methylcellulose | 2.25 kg |
| Purified water | 40 kg |
| Separating layer | |
| Core material | 15.00 kg |
| Hydroxypropyl cellulose | 1.50 kg |
| Talc | 2.57 kg |
| Magnesium stearate | 0.21 kg |
| Purified water | 30 kg |
| Enteric coating layer | |
| Pellets covered with separating layer | 18.00 kg |
| Methacrylic acid copolymer | 9.00 kg |
| Triethyl citrate | 2.70 kg |
| Mono- and diglycerides | 0.45 kg |
| Polysorbate 80 | 0.04 kg |
| Purified water | 19 kg |
| Tablets | |
| Enteric coating layered pellets | 6.00 kg |
| Microcrystalline cellulose | 13.95 kg |
| Sodium stearyl fumarate | 0.05 kg |

Suspension layering is performed in a fluid bed apparatus using bottom spray technique. Magnesium omeprazole is sprayed onto sugar sphere seeds from a water suspension containing the dissolved binder. The size of sugar sphere seeds are in the range of 0.25 to 0.35 mm.

The prepared core material is covered with separating layer in a fluid bed apparatus with a hydroxypropyl cellulose solution containing talc and magnesium stearate. The enteric coating layer consisting of methacrylic acid copolymer, mono- and diglycerides, triethyl citrate and polysorbate is sprayed as a dispersion onto the pellets covered with separating layer in a fluid bed apparatus. The Vickers hardness on enteric coating layered pellets prepared is measured to a value of 2.

The enteric coating layered pellets are classified by sieving. Enteric coating layered pellets, microcrystalline cellulose and sodium stearyl fumarate are mixed and compressed into tablets using a rotary tableting machine equipped with 36 pairs of 8 mm round punches. The amount of omeprazole in each tablet is approx. 10 mg, tableting speed 110 000 tablets per hour and an upper punch force of 10 kN is used. Tablet hardness measured on a Schleuniger hardness tester is 55–65N.

Example 3

| Core material | |
|---|---|
| Magnesium omeprazole | 1 500 g |
| Sugar sphere seeds (non-pareils) | 1 500 g |
| Hydroxypropyl methylcellulose | 420 g |
| Colloidal silicon dioxide | 8 g |
| Purified water | 4 230 g |
| Separating layer | |
| Core material | 500 g |
| Hydroxypropyl cellulose | 40 g |
| Talc | 67 g |
| Magnesium stearate | 6 g |
| Purified water | 800 g |

-continued

| Enteric coating layer | |
|---|---|
| Pellets covered with separating layer | 500 g |
| Methacrylic acid copolymer | 200 g |
| Triethyl citrate | 60 g |
| Purified water | 392 g |
| Tablets | |
| Enteric coating layered pellets | 430 g |
| Microcrystalline cellulose | 871 g |
| Sodium stearyl fumarate | 3 g |

Magnesium omeprazole, part of the hydroxypropyl methylcellulose and colloidal silicon dioxide are dry-mixed forming a powder mixture. Sugar sphere seeds (0.25–0.35 mm) are layered with the powder in a centrifugal fluidized coating granulator while spraying a hydroxypropyl methylcellulose solution (6%, w/w).

The prepared core material is dried and covered with separating layer in a centrifugal fluidized coating granulator. A fluid bed apparatus is used for enteric coating layering.

Enteric coating layered pellets, microcrystalline cellulose and sodium stearyl fumarate are mixed and compressed into tablets using a rotary tableting machine equipped with 6 pairs of 10 mm round punches. The amount of omeprazole is approx. 20 mg. Hardness of prepared tablets measured on a Schleuniger hardness tester is determined to 130–140N.

Example 4

| Core material | |
|---|---|
| Magnesium omeprazole | 8.00 kg |
| Silicon dioxide seeds | 8.00 kg |
| Hydroxypropyl methylcellulose | 1.41 kg |
| Sodium lauryl sulfate | 0.08 kg |
| Purified water | 28 kg |
| Separating layer | |
| Core material | 10.00 kg |
| Hydroxypropyl methylcellulose | 0.80 kg |
| Purified water | 10 kg |
| Enteric coating layer | |
| Pellets covered with separating layer | 300 g |
| Methacrylic acid copolymer | 124 g |
| Polyethylene glycol 400 | 25 g |
| Mono- and diglycerides | 3 g |
| Polysorbate 80 | 1 g |
| Purified water | 463 g |
| Tablets | |
| Enteric coating layered pellets | 200 g |
| Microcrystalline cellulose | 598 g |
| Sodium stearyl fumarate | 2 g |

Suspension layering is performed in a fluid bed apparatus. Magnesium omeprazole is sprayed onto the seeds of silicon dioxide (size range 0.15–0.3 mm) from a water suspension containing the dissolved binder and a surface active ingredient.

The prepared core material is covered with separating layer in a fluid bed apparatus using a hydroxypropyl methylcellulose solution. The enteric coating layer material is sprayed as a water dispersion onto pellets in a fluid bed apparatus. The Vicker hardness on enteric coating layered pellets is measured to a value of 3.

Enteric coating layered pellets and the tableting excipients are mixed and compressed into tablets as described in Example 1.

Example 5

| Enteric coating layer | |
|---|---|
| Pellets covered with separating layer (manufacturing and composition as in Example 1) | 500 g |
| Methacrylic acid copolymer | 250 g |
| Polyethylene glycol 6000 | 75 g |
| Mono- and diglycerides | 12.5 g |
| Polysorbate 80 | 1.2 g |
| Purified water | 490 g |
| Tablets | |
| Enteric coating layered pellets | 600 g |
| Microcrystalline cellulose | 1 395 g |
| Sodium stearyl fumarate | 5 g |

Enteric coating layered pellets with a measured Vickers value of 2, microcrystalline cellulose and sodium stearyl fumarate are mixed and compressed into tablets as described in Example 3.

Example 6

| Enteric coating layer | |
|---|---|
| Pellets covered with separating layer (manufacturing and composition as in Example 2) | 500 g |
| Hydroxypropyl methylcellulose phthalate | 400 g |
| Diethyl phthalate | 80 g |
| Ethanol | 1 600 g |
| Acetone | 4 000 g |
| Tablets | |
| Enteric coating layered pellets | 500 g |
| Microcrystalline cellulose | 1 500 g |
| Magnesium stearate | 5 g |

Enteric coating layering is performed by spaying a solution in a fluid bed. Enteric coating layered pellets, microcrystalline cellulose and magnesium stearate are mixed and compressed into tablets as in Example 3.

Example 7

| Tablets | |
|---|---|
| Enteric coating layered pellets (manufacturing and composition as in Example 2) | 1.00 kg |
| Dibasic calcium phosphate anhydrous | 1.76 kg |
| Microcrystalline cellulose | 0.44 kg |
| Magnesium stearate | 0.016 kg |

Enteric coating layered pellets, dibasic calcium phosphate anhydrous in granulated form, microcrystalline cellulose and magnesium stearate are mixed and compressed into tablets as described in Example 3. Upper punch force is set to approx. 30 kN.

Example 8

| Core material | |
|---|---|
| (−)-Omeprazole | 600 g |
| Sugar sphere seeds | 300 g |
| Povidone | 100 g |
| Purified water | 2000 g |

-continued

| Enteric coating layer | |
|---|---|
| Core material | 600 g |
| Methacrylic acid copolymer | 400 g |
| Triethyl citrate | 120 g |
| Talc | 120 g |
| Tablets | |
| Enteric coating layered pellets | 1 000 g |
| Microcrystalline cellulose | 1 450 g |
| Anhydrous lactose | 140 g |
| Starch | 230 g |
| Povidone | 180 g |
| Purified water | 836 g |

(−)-Omeprazole is sprayed onto sugar sphere seeds from a water suspension containing the dissolved binder in a fluid bed apparatus. The enteric coating layer consisting of methacrylic acid copolymer, triethyl citrate and talc is sprayed as a disperssion onto the core material in a fluid bed apparatus. The tablet excipient povidone is dissolved in water. Microcrystalline cellulose, anhydrous lactose and starch are dry-mixed. The povidone solution is added while wet-mixing. The wet mass is dried in an oven. The granulated mass is milled using an oscillating granulator.

Enteric coating layered pellets and the prepared granulate are mixed and compressed into engraved and scored tablets using a rotary tableting machine equipped with 16 pairs of oval, 8.5×17 mm, tablet punches.

Example 9

| Over-coating layer | |
|---|---|
| Enteric coating layered pellets (manufacturing and composition as in Example 2) | 400 g |
| Hydroxypropyl methylcellulose | 120 g |
| Purified water | 2280 g |
| Tablets | |
| Over-coating layered pellets | 100 g |
| Microcrystalline cellulose | 233 g |

In a fluid bed apparatus a hydroxypropyl methylcellulose solution is sprayed onto enteric coating layered pellets. Vickers hardness measured on the enteric coating layered pellets before applying the over-coating layer is determined to 2 and the Vickers hardness measured on the over-coating layered pellets is determined to 11. Pellets covered with over-coating layer and microcrystalline cellulose are mixed and compressed into tablets as in Example 1. Hardness of tablets measured on a Schleuniger tablet hardness tester is determined to 170–190N.

Example 10

| Core material | |
|---|---|
| Omeprazole | 225 g |
| Mannitol | 1425 g |
| Hydroxypropyl cellulose | 60 g |
| Microcrystalline cellulose | 40 g |
| Anhydrous lactose | 80 g |
| Sodium lauryl sulfate | 5 g |
| Dibasic sodium phosphate dihydrate | 8 g |
| Purified water | 350 g |

| Separating layer | |
|---|---|
| Core material | 300 g |
| Hydroxypropyl cellulose | 30 g |
| Talc | 51 g |
| Magnesium stearate | 4 g |
| Water | 600 g |
| Enteric coating layer | |
| Pellets covered with separating layer | 279 g |
| Methacrylic acid copolymer | 140 g |
| Triethyl citrate | 42 g |
| Mono- and diglycerides | 7 g |
| Polysorbate 80 | 0.7 g |
| Water | 300 g |
| Tablets | |
| Enteric coating layered pellets | 352 g |
| Microcrystalline cellulose | 1 052 g |
| Sodium stearyl fumarate | 3 g |

The dry ingredients for producing the core material are well mixed in a mixer. The granulation liquid is added and the mixture is kneaded and granulated to a proper consistency. The wet mass is pressed through an extruder screen. The granules are converted into a spherical form in a spheronizer. The core material is dried in a fluid bed apparatus and classified into a suitable particle size range, 0.7–1.0 mm.

Prepared core material is covered with separating layer and enteric coating layer as in Example 2. Enteric coating layered pellets, microcrystalline cellulose and sodium stearyl fumarate are mixed and compressed into tablets as described in Example 3.

Example 11

| Enteric coating layer | |
|---|---|
| Core material (no separating layer) | 500 g |
| Methacrylic acid copolymer | 500 g |
| Triethyl citrate | 150 g |
| Mono- and diglycerides | 25 g |
| Polysorbate 80 | 2.5 g |
| Purified water | 978 g |
| Tablets | |
| Enteric coating layered pellets | 800 g |
| Microcrystalline cellulose | 1 860 g |
| Sodium stearyl fumarate | 7 g |

Core material is produced as in Example 2. Enteric coating layered pellets and tablet excipients are compressed as described in Example 3. The dose of omeprazol in each tablet corresponds to 20 mg. Measured tablet hardness is 80–100N.

Example 12

| Core material | |
|---|---|
| Sodium omeprazole | 326 g |
| Sugar sphere seeds | 300 g |
| Hydroxypropyl cellulose | 80 g |
| Purified water | 1 520 g |
| Separating layer | |
| Core material | 300 g |

-continued

| | |
|---|---|
| Hydroxypropyl cellulose | 21 g |
| Talc | 37 g |
| Magnesium stearate | 5 g |
| Purified water | 400 g |
| Enteric coating layer | |
| Pellets covered with separating layer | 270 g |
| Methacrylic acid copolymer | 256 g |
| Polyethylene glycol 400 | 64 g |
| Purified water | 1 217 g |
| Tablets | |
| Enteric coating layered pellets | 100 g |
| Microcrystalline cellulose | 200 g |
| Sodium stearyl fumarate | 1 g |

To produce core material, solution layering is performed in a fluid bed apparatus. Sodium omeprazole is sprayed onto sugar sphere seeds from a water solution containing the dissolved binder.

The prepared core material is covered with separating layer in a fluid bed apparatus with a hydroxypropyl cellulose solution containing talc and magnesium stearate. The enteric coating layer material is sprayed as a dispersion onto the pellets covered with separating layer in a fluid bed apparatus.

Enteric coating layered pellets and tablet excipients are compressed into tablets as described in Example 1. The amount of sodium omeprazole in each tablet is approx. 15 mg.

Example 13

| | |
|---|---|
| Core material | |
| Magnesium omeprazole | 15.0 kg |
| Sugar sphere seeds (0.25–0.35 mm) | 15.0 kg |
| Hydroxypropyl methylcellulose | 2.25 kg |
| Purified water | 45 kg |
| Separating layer | |
| Core material | 30.0 kg |
| Hydroxypropyl cellulose | 3.00 kg |
| Talc | 5.14 kg |
| Magnesium stearate | 0.43 kg |
| Purified water | 60 kg |
| Enteric coating layer | |
| Pellets covered with separating layer | 200 g |
| Hydroxypropyl methylcellulose acetate succinate | 100 g |
| Triethyl citrate | 30 g |
| Purified water | 309 g |
| Ethanol | 720 g |
| Tablets | |
| Enteric coating layered pellets | 100 g |
| Microcrystalline cellulose | 227 g |
| Crospovidone | 5 g |
| Sodium stearyl fumarate | 1 g |

The pellets covered with separating layer are produced as in Example 2. The enteric coating layer is applied in a fluid bed from a water/ethanol solution. The Vickers hardness of the enteric coating layered pellets is measured to a value of 5. Enteric coating layered pellets and tablet excipients are mixed and compressed into tablets as described in Example 1.

Example 14

| | |
|---|---|
| Enteric coating layer | |
| Pellets covered with separating layer | 200 g |
| Methacrylic acid copolymer | 200 g |
| Triethyl citrate | 60 g |
| Mono- and diglycerides | 10 g |
| Polysorbate 80 | 1 g |
| Purified water | 391 g |
| Over-coating layer | |
| Enteric coating layered pellets | 471 g |
| Hydroxypropyl methylcellulose | 6 g |
| Magnesium stearate | 0.2 g |
| Purified water | 120 g |
| Tablets | |
| Over-coating layered pellets | 140 g |
| Microcrystalline cellulose | 114 g |
| Sodium stearyl fumarate | 0.4 g |

Pellets covered with separating layer are produced according to Example 13. The enteric coating layer and the over-coating layer are sprayed onto pellets in a fluid bed apparatus. Over-coating layered pellets and tablet excipients are compressed using a single punch (round, 12 mm) tableting machine.

Example 15

| | |
|---|---|
| Enteric coating layer | |
| Pellets covered with separating layer | 200 g |
| Methacrylic acid copolymer | 40 g |
| Triethyl citrate | 12 g |
| Mono- and diglycerides | 2 g |
| Polysorbate 80 | 0.2 g |
| Purified water | 78 g |
| Over-coating layer | |
| Enteric coating layered pellets | 200 g |
| Hydroxypropyl methylcellulose | 4 g |
| Magnesium stearate | 0.1 g |
| Tablets | |
| Over-coating layered pellets | 69 g |
| Microcrystalline cellulose | 230 g |
| Sodium stearyl fumarate | 0.7 g |

Pellets covered with separating layer are produced according to Example 13. The enteric coating layer and the over-coating layer are sprayed onto pellets in a fluid bed apparatus. The amount of enteric coating layer material corresponds to an enteric coating layer thickness of approx. 20 μm. Over-coating layered pellets and tablet excipients are compressed using a single punch (round, 10 mm) tableting machine. Tablet weight approx. 332 mg, and hardness 70–77N.

Example 16

| | |
|---|---|
| Core material | |
| (–)-omeprazole magnesium | 300 g |
| Sugar sphere seeds | 300 g |
| Hydroxypropyl methylcellulose | 75 g |
| Purified water | 1 425 g |

-continued

| Separating layer | |
|---|---|
| Core material | 295 g |
| Hydroxypropyl cellulose | 29.5 g |
| Talc | 50.6 g |
| Magnesium stearate | 4.2 g |
| Purified water | 590 g |
| Enteric coating layer | |
| Pellets covered with separating layer | 300 g |
| Methacrylic acid copolymer | 120 g |
| Triethyl citrate | 36 g |
| Mono- and diglycerides | 6 g |
| Polysorbate 80 | 0.6 g |
| Purified water | 235 g |
| Tablets | |
| Enteric coating layered pellets | 150 g |
| Microcrystalline cellulose | 342 g |
| Crospovidone | 7 g |
| Sodium stearyl fumarate | 0.7 g |

The enteric coating layered pellets are produced in a fluid bed apparatus. Enteric coating layered pellets and tablet excipients are mixed and compressed into tablets as described in Example 1.

Example 17

| Enteric coating layer | |
|---|---|
| Pellets covered with separating layer | 500 g |
| Cellulose acetate phtalate | 375 g |
| Diethyl phthalate | 150 g |
| Acetone | 2 000 g |
| Ethanol | 2 000 g |
| Over-coating layer | |
| Enteric coating layered pellets | 500 g |
| Povidone | 10 g |
| Purified water | 200 g |
| Tablets | |
| Over-coating layered pellets | 100 g |
| Microcrystalline cellulose | 300 g |
| Crospovidone | 8 g |
| Sodium stearyl fumarate | 1 g |

The pellets covered with separating layer are produced as in Example 2. The enteric coating layer is applied in a fluid bed from an acetone/ethanol solution. Over-coating layered pellets and tablet excipients are mixed and compressed into tablets as described in Example 1.

The results from tests on acid resistance of the enteric coating layered pellets and the compressed tablets are disclosed in Table I, below.

TABLE I

| Example No | Acid resistance, pellets (%) | Acid resistance, tablets (%) |
|---|---|---|
| 1 | 91 | 90 |
| 2 | 99 | 96 |
| 3 | 96 | 90 |
| 4 | 91 | 90 |
| 5 | 94 | 96 |
| 7 | 95 | 97 |
| 9 | 96 | 95 |
| 10 | 97 | 88 |
| 11 | 94 | 93 |

TABLE I-continued

| Example No | Acid resistance, pellets (%) | Acid resistance, tablets (%) |
|---|---|---|
| 13 | 98 | 95 |
| 14 | 99 | 95 |
| 15 | 98 | 94 |
| 16 | 97 | 94 |

Comments

Surprisingly, the acid resistance, tablets, shows that the enteric coating layer according to the present invention sufficiently withstands compression.

Example 7. Due to poor compressability the punch force has to be set very high. Surprisingly there is no reduction in acid resistance after compression.

Reference Example I

| Tablets | |
|---|---|
| Omeprazole enteric coating layered pellets | 180 g |
| Microcrystalline cellulose | 219 g |
| Sodium stearyl fumarate | 1 g |

Omeprazole pellets from Losec® 40 mg capsules are mixed with microcrystalline cellulose and sodium stearyl fumarate and compressed into tablets using a single punch tableting machine. The Vickers hardness on the enteric coating layered pellets is measured to a value of 22. The tablet tooling is round with a diameter of 10 mm. Punch force is set to 3.7 kN.

Reference Example II

| Tablets | |
|---|---|
| Lansoprazole enteric coating layered pellets (content of Lanzo ® 30 mg capsules) | 276 g |
| Microcrystalline cellulose | 644 g |

Lansoprazole pellets are mixed with microcrystalline cellulose and tableted in a single punch tableting machine. The Vickers hardness on enteric coating layered pellets is measured to a value of 18. The tablet tooling is round with a diameter of 12 mm. Punch force is set to 3.6 kN.

Reference Example III

| Core material | |
|---|---|
| Magnesium omeprazole | 15.0 kg |
| Sugar sphere seeds | 15.0 kg |
| Hydroxypropyl methylcellulose | 2.25 kg |
| Purified water | 40 kg |
| Separating layer | |
| Core material | 15.0 kg |
| Hydroxypropyl cellulose | 1.5 kg |
| Talc | 2.57 kg |
| Magnesium stearate | 0.21 kg |
| Purified water | 30 kg |
| Enteric coating layer | |
| Pellets covered with separating layer | 200 g |

-continued

| | |
|---|---|
| Enteric coating layer material is used as described in Drugs Made In Germany 37, No. 2 (1994), p. 53, Table 1, Formulation no. 9. The amount of coating polymer as calculated in above reference is 40% (w/w). | |
| Over-coating layer | |
| Enteric coating layered pellets | 291 g |
| Hydroxypropyl methylcellulose | 4 g |
| Magnesium stearate | 0.2 g |
| Purified water | 80 g |
| Tablets | |
| Over-coating layered pellets | 75 g |
| Microcrystalline cellulose | 174 g |
| Sodium stearyl fumarate | 0.6 g |

Suspension layering is performed in a fluid bed apparatus. Omeprazol magnesium is sprayed onto sugar sphere seeds from a water suspension containing the dissolved binder. The separating layer, enteric coating layer and the over-coating layer are sprayed onto pellets in a fluid bed apparatus. The over-coating layer is applied to prevent sticking of pellets before tableting. Over-coating layered pellets and tablet excipients are tableted as in Example 1. Upper punch force is set to 5 kN.

The results from tests on acid resistance of the enteric coating layered pellets and the compressed tablets are disclosed in Table II, below.

TABLE II

| Reference example number | Acid resistance pellets (%), | Acid resistance tablets (%), |
|---|---|---|
| I | 97 | 6 |
| II | 98 | 25 |
| III | 98 | 82 |

Comments

As can be seen from the presented data, the enteric coating layer of the products studied, including the two marketed products (Reference examples I and II) do not possess the mechanical properties required to withstand compression into tablets.

Preparation of Active Substance

Magnesium omeprazole used in some of the Examples is produced in accordance with the process given in WO 95/01977, cited above. Omeprazole used in Example 10 is disclosed in EP-A1-0005129, hereby incorporated in a whole by reference. Sodium omeprazole sodium used in Example 12 is disclosed in EP-AI-0124495, hereby incorporated in a whole as reference. The single enantiomers of omeprazole salts used for instance in Example 16, are produced in accordance with the processes given in WO 94/27988, cited above and preferably as described in Examples A and B below.

Example A. Preparation of (−)-omeprazole magnesium salt

Magnesium (0.11 g, 4.5 mmol) was dissolved and reacted with methanol (50 ml) at 40° C. with a catalytic amount of methylene chloride. The reaction was run under nitrogen and was finished after five hours. At room temperature a mixture of the two enantiomers [90%(−)-isomer and 10%(+)-isomer] of 5-methoxy-2-[[(4-methoxy-3,5-dimethyl-2-pyridinyl) methyl]sulfinyl]-1H-benzimidazole (2.84 g, 8.2 mmol) was added to the magnesium methoxide solution. The mixture was stirred for 12 hours whereupon a small amount of water (0.1 ml) was added in order to precipitate inorganic magnesium salts. After 30 minutes stirring, these inorganic salts were filtered off and the solution was concentrated on a rotavapor. The residue was now a concentrated methanolic solution of the enantiomeric mixture (i.e. the title compound contaminated with the (+)-isomer), with an optical purity (enantiomeric excess, e.e.) of 80%. This mixture was diluted with acetone (100 ml) and after stirring at room temperature for 15 minutes, a white precipitate was obtained. Additional stirring for 15 minutes and thereafter filtration afforded 1.3 g (50%) of the title compound as white crystals. Chiral analyses of the crystals and mother liquor were performed by chromatography on an analytical chiral column. The optical purity of the crystals and mother liquor was found to be 98.4 e.e. and 64.4% e.e., respectively. Thus, the optical purity (e.e.) has been enhanced from 80% to 98.4% simply by crystallising the Mg-salt from a mixture of acetone and methanol. The product was crystalline as shown by powder X-ray diffraction and the magnesium content was 3.44% as shown by atomic absorption spectroscopy. $[\alpha]_D^{20} = -131.5°$ (c=0.5%, methanol).

Example B. Preparation of (+)-omeprazole magnesium salt

Magnesium (0.11 g, 4.5 mmol) was dissolved and reacted with methanol (50 ml) at 40° C. with a catalytic amount of methylene chloride. The reaction was run under nitrogen and was finished after five hours. At room temperature a mixture of the two enantiomers [90%(+)-isomer and 10%(−)-isomer] of 5-methoxy-2-[[(4-methoxy-3,5-dimethyl-2-pyridinyl) methyl]sulfinyl]-1H-benzimidazole (2.84 g, 8.2 mmol) was added to the magnesium methoxide solution. The mixture was stirred for 12 hours whereupon a small amount of water (0.1 ml) was added in order to precipitate inorganic magnesium salts. After 30 minutes stirring, these inorganic salts were filtered off and the solution was concentrated on a rotavapor. The residue was now a concentrated methanolic solution of the enantiomeric mixture (i.e. the title compound contaminated with the (−)-isomer), with an optical purity (e.e.) of 80%. This mixture was diluted with acetone (100 ml) and after stirring at room temperature for one hour, a white precipitate was obtained. Additional stirring for 30 minutes and thereafter filtration afforded 0.35 g of the title compound as white crystals. Additional stirring of the mother liquor for 24 hours at room temperature afforded another 1.0 g (total yield=52%). Chiral analyses of the crystals and the second mother liquor were performed by chromatography on an analytical chiral column. The optical purity of the first crystals was 98.8% e.e. and 99.5% ee., respectively. The optical purity of the mother liquor was found to be 57% e.e. Thus, the optical purity (e.e.) has been enhanced from 80% to approximately 99% simply by crystallising the Mg-salt from a mixture of acetone and methanol. The first precipitation was crystalline as shown by powder X-ray diffraction and the magnesium content of the same fraction was 3.49% as shown by atomic absorption spectroscopy. $[\alpha]_D^{20} = +135.6°$ (c=0.5%, methanol).

What is claimed is:

1. A pharmaceutical multiple unit tablet composition for oral treatment of gastrointestinal disorder comprising:
   at least one tablet excipient; and
   a multiple of a pellet or granule, the pellet or granule ranging between 0.1 mm and 2 mm in size and comprising an active ingredient selected from the group consisting of omeprazole, a single enantiomer of omeprazole, an alkaline salt of omeprazole, and an alkaline salt of a single enantiomer of omeprazole; and the pellet or granule being covered with at least one enteric coating layer comprising a plasticizing compound in the amount of more than about 20% to less than about 50% by weight of the enteric coating layer polymer so as to minimize the reduction of acid resistance of the enteric coating layered units upon compression into the tablet form.

2. The composition according to claim 1, wherein the acid resistance of the individually enteric coating layered units is in coherence with the requirements on enteric coated articles defined in the United States Pharmacopeia.

3. The composition according to claim 1, wherein the acid resistance of the individually enteric coating layered units does not decrease more than 10% during the compression of the individual units into the multiple unit tableted dosage form.

4. The tablet composition according to claim 1 wherein the enteric coating layer or a multiple thereof comprises a thickness of at least 10 μm.

5. The tablet composition according to claim 1 wherein each enteric coating layered unit is covered with an over-coating layer comprising a pharmaceutically acceptable excipient.

6. The tablet composition according to claim 1 wherein the pellet or granule further comprises at least one alkaline compound.

7. The composition according to claim 1, wherein the active ingredient is a magnesium salt of omeprazole having a degree of crystallinity which is higher than 70% as determined by X-ray powder diffraction.

8. The composition according to claim 1, wherein the active ingredient is an alkaline salt of (+)-omeprazole or (−)-omeprazole.

9. The composition according to claim 1, wherein the multiple unit form is divisible.

10. The composition according to claim 1, wherein the multiple unit form is dispersible to a suspension of individually enteric coating layered units in an aqueous liquid.

11. A process for the manufacture of the oral pharmaceutical composition according to claim 1 comprising the following steps:
(a) Shaping a multiple of a pellet or granule comprising an active ingredient selected from the group consisting of omeprazole, a single enantiomer of omeprazole, an alkaline salt of omeprazole, and an alkaline salt of a single enantiomer of omeprazole;
(b) covering the pellet or granule of step (a) with at least one enteric coating layer having advantageous mechanical properties;
(c) mixing a multiple of the enteric coating layered pellet or granule of step (b) with at least one tablet excipient; and
(d) compressing the mixture into, tablet form without significantly affecting the acid resistance of the enteric coating layered units due to the advantageous mechanical properties of the enteric coating.

12. The composition according to claim 11, wherein the pellet or granule comprises a seed layered with the active ingredient.

13. The composition according to claim 12, wherein the seeds have a size of 0.1–2 mm.

14. A process according to claim 11, wherein the individually enteric coating layered units are further coated with an over-coating layer.

15. A method for inhibiting gastric acid secretion in mammals and man comprising administering to a host in a need thereof a therapeutically effective dose of the composition according to claim 1.

16. A method for the treatment of gastrointestinal inflammatory diseases in mammals and man comprising administering to a host in a need thereof a therapeutically effective dose of the composition according to claim 1.

17. A press-through blister package comprising at least one press-through blister; comprising a pharmaceutical multiple unit tablet of the composition according to claim 1.

18. The composition according to claim 1 wherein the alkaline salt is a magnesium salt.

19. The composition according to claim 18 wherein the separating layer further comprises at least one alkaline compound.

20. The process according to claim 11, wherein the pellet or granule further comprises at least one alkaline compound.

21. The process according to claim 11, further comprising the step of covering the pellet or granule of step (a) with a separating layer or a multiple thereof.

22. The tablet composition according to claim 1, wherein the pellet or granule is further covered by at least one separating layer which comprises a pharmaceutically acceptable excipient which is soluble, or insoluble but disintegrating in water, the separating layer being located under the enteric coating layer.

23. The composition according to claim 1, wherein the enteric coating layer applied to a pellet or granule has a Vickers hardness value of less than 8.

24. The process according to claim 11, wherein the enteric coating layer covering the pellet or granule has a thickness of at least 10 μm.

25. The process according to claim 11, wherein the pellet or granule of step (a) is shaped by layering the active ingredient on a seed ranging in size from about 0.1 to about 2.0 mm.

* * * * *

UNITED STATES PATENT AND TRADEMARK OFFICE
CERTIFICATE OF CORRECTION

PATENT NO. : 5,817,338
DATED : October 6, 1998
INVENTOR(S) : Bergstrand et al.

It is certified that error appears in the above-indentified patent and that said Letters Patent is hereby corrected as shown below:

Claim 12 at column 22, line 6, "claim 11" should be -- claim 1 --.

Claim 19 at column 22, line 28, "claim 18" should be -- claim 22 --.

Signed and Sealed this

Eleventh Day of May, 1999

Attest:

Q. TODD DICKINSON

Attesting Officer

Acting Commissioner of Patents and Trademarks